United States Patent [19]
Rice et al.

[11] Patent Number: 5,217,486
[45] Date of Patent: Jun. 8, 1993

[54] SUTURE ANCHOR AND INSTALLATION TOOL

[75] Inventors: John T. Rice, Lincoln; Richard F. Wenstrom, Jr., Attleboro, both of Mass.

[73] Assignee: Mitek Surgical Products, Inc., Norwood, Mass.

[21] Appl. No.: 837,061

[22] Filed: Feb. 18, 1992

[51] Int. Cl.⁵ ............................................. A61B 17/00
[52] U.S. Cl. ..................................... 606/232; 606/72; 606/220
[58] Field of Search ................. 606/220, 232, 72, 139, 606/144, 75, 78; 604/59

[56] References Cited

U.S. PATENT DOCUMENTS

| | | | |
|---|---|---|---|
| 4,060,083 | 11/1977 | Hanson | 604/59 |
| 4,669,473 | 6/1987 | Richards et al. | 606/220 |
| 4,721,103 | 1/1988 | Freedland | 606/72 |
| 4,741,330 | 5/1988 | Hayhurst | 606/232 |
| 4,946,468 | 8/1990 | Li | 606/232 |
| 4,968,315 | 11/1990 | Gatturna | 606/232 |
| 5,041,129 | 8/1991 | Hayhurst et al. | 606/232 |
| 5,046,513 | 9/1991 | Gatturna et al. | 606/232 |

Primary Examiner—Stephen C. Pellegrino
Assistant Examiner—Gary Jackson
Attorney, Agent, or Firm—Pandiscio & Pandiscio

[57] ABSTRACT

A system for attaching an object to a workpiece including an anchor and an installation tool is provided. The anchor includes a body having a transverse cross-section slightly smaller than the transverse cross-section of a hole in a surface of the workpiece in which it is to be deployed, and at least two barbs. The body has a distal portion having an inner end, a proximal portion having an inner end, and a middle portion connecting the inner ends of the distal and proximal portions respectively. The barbs extend from the first end of the distal portion axially and radially outwardly to outer ends located radially outwardly of an axial projection of the maximum transverse cross-section of the distal portion. The barbs are located in channels having bases which extend parallel to the longitudinal axis of the body in the middle section and thereafter slant outwardly relative to the longitudinal axis of the body as they extend to the outer end of the proximal portion. Each barb is curved in its normal unstressed state, but is capable of being deformed into a substantially straight configuration. The anchor assembly is deployed by an installation tool which includes an elongated shaft having a distal end and a proximal end, tubular means associated with said distal end of said shaft adapted to receive and hold said middle and proximal portions of said anchor body, and plunger means adapted for engagement with said outer end of said proximal portion of said anchor body, said plunger means being axially movable through said tubular means so as to expell said anchor from said tubular means and to drive said anchor into said hole. A method of attaching an object to a workpiece utilizing such anchors and installation tools also is provided.

36 Claims, 4 Drawing Sheets

SUTURE ANCHOR AND INSTALLATION TOOL

FIELD OF THE INVENTION

The present invention relates generally to fastening devices. More particularly, the present invention relates to anchoring devices for fixedly attaching an object to a workpiece, and installation tools for deploying such anchoring devices. Still more particularly, the present invention relates to suture anchors for anchoring a portion of a piece of conventional suture in bone, and installation tools for deploying such anchors.

BACKGROUND OF THE INVENTION

In U.S. Pat. No. 4,898,156, entitled "Suture Anchor"; U.S. Pat. No. 4,899,743, entitled "Suture Anchor Installation Tool"; U.S. Pat. No. 4,946,468, entitled "Suture Anchor and Suture Anchor Installation Tool"; U.S. Pat. No. 4,968,315, entitled "Suture Anchor and Suture Anchor Installation Tool"; U.S. Pat. No. 5,002,550, entitled "Suture Anchor Installation Tool"; U.S. Pat. No. 5,046,513, entitled "Method For Anchoring Suture To Bone"; and U.S. Pat. application Ser. No. 07/766,025, filed Sep. 26, 1991, entitled "Suture Anchor and Installation Tool", there are disclosed a variety of anchors for anchoring a portion of a piece of conventional suture in bone. The foregoing patents and patent application further disclose several installation tools for deploying the anchors disclosed therein. Complete details of the construction and operation of these suture anchors and installation tools are provided in the above-identified patents and patent application, which patents and patent application are hereby incorporated herein by reference.

It will, therefore, be understood that suture anchors of the sort comprising a coupling member and at least one elastically deformable, normally curved barb member extending outwardly from the coupling member are known in the art. It will also be understood that installation tools for deploying such suture anchors in holes formed in workpieces (e.g. bone) are similarly known in the art.

As the requirements of users of such devices have become more demanding, however, known suture anchors and known suture anchor installation tools have encountered several problems. More particularly, it has been found that there is a growing desire in the medical field to anchor suture to smaller and smaller bones, and hence to deploy smaller and smaller suture anchor in smaller and smaller holes formed in those bones.

Until now, however, two primary factors have tended to limit the extent to which it was possible to reduce the size of both the suture anchors and also the size of the anchor-receiving holes.

First, the suture anchor's coupling member, which forms the body of the anchor, must include sufficient material to ensure the structural integrity of the anchor. In addition, the suture anchor's coupling member must include means for attaching the suture to the anchor, and means for engaging the anchor with its associated insertion tool. At the same time, of course, the anchor-receiving holes must be formed large enough to accommodate the suture anchors therein. Thus, those factors which tend to limit the downsizing of suture anchor bodies also tend to limit the downsizing of anchor-receiving holes.

Secondly, known suture anchor installation tools are designed to operate so that the portion of the installation tool which engages and carries the anchor remains in engagement with the anchor the entire time that the anchor is moving to its desired location within the bone. With such prior art designs, the engaging and carrying portion of the installation tool separates from the anchor only after the anchor has been deployed in the bone. Thus, with prior art designs, the anchor-receiving holes must be formed large enough to receive not only the suture anchor but also the engaging and carrying portion of the installation tool as well.

Accordingly, while various suture anchor designs and installation tool designs have been disclosed in the aforementioned patents and patent application, including (a) the alternative of moving the suture attachment means from the distal end of the coupling member toward the proximal end of the coupling member so that the suture need not pass by the outside of the coupling member to reach the exterior of the bone, and hence the anchor-receiving hole can generally be formed somewhat smaller, and (b) the alternative of reducing the diameter of the proximal end of the coupling member relative to the remainder of the coupling member so that the proximal end of the coupling member can be received by an installation tool, while at the same time forming the installation tool so that it has an outside diameter no larger than the largest diameter of the coupling member, there are practical limits to the effectiveness of these prior art constructions as suture anchor sizes and bone hole sizes become smaller and smaller. Among other things, the attachment means for attaching the suture to the anchor generally requires the presence of sufficient coupling member material at the point of attachment to ensure that the suture will not break free from the coupling member. For example, if the attachment means comprises a hole formed in the reduced diameter proximal portion of the coupling member, it will be appreciated that the diameter of the reduced diameter proximal portion of the coupling member must always significantly exceed the diameter of the suture so as to ensure proper structural integrity. Similarly, as long as that portion of the insertion tool which engages and carries the suture anchor must also enter the bone hole so as to move the suture anchor to its desired location in the bone, there are practical limits as to how small the insertion tool's shaft may be formed without creating problems in mounting the suture anchor to the installation tool, and without creating bending problems in the shaft when driving suture anchors into bone.

OBJECTS AND SUMMARY OF THE INVENTION

Accordingly, one object of the present invention is to provide an improved anchor and installation tool system, wherein the components of the system are adapted for effective use in smaller holes in workpieces.

Another object of the present invention is to provide an improved anchor configuration which is adapted for effective anchoring disposition within smaller holes in workpieces.

Yet another object of the present invention is to provide an improved installation tool wherein that portion of the tool which engages and carries the anchor to the hole in the workpiece need not enter the hole in order for the anchor to be effectively deployed in the workpiece.

Another object of the present invention is to provide a novel anchoring system which minimizes the size requirements for the workpiece holes yet still allows effective anchor deployment.

And another object of the present invention is to provide an anchor and an installation tool which improve upon the anchors and installation tools disclosed in the above-identified patents and patent application.

Yet another object of the present invention is to provide a novel method for deploying an anchor within a hole in a workpiece.

And another object of the present invention is to provide a novel suture anchor and a novel suture anchor installation tool for attaching a suture to a bone.

These and other objects of the invention are achieved through the provision and use of a novel anchoring system which comprises a novel anchor and a novel installation tool.

The novel anchor includes a coupling member, at least two barbs, and attachment means.

The coupling member comprises a body having a longitudinal axis. The body includes a distal portion having an inner end and an outer end, a proximal portion having an inner end and an outer end, and a middle portion connecting the inner end of the distal portion to the inner end of the proximal portion. The body has a maximum cross-section, as measured transverse to its longitudinal axis, which is slightly smaller than the diameter of the hole in the workpiece within which the anchor is to be deployed. At least two equally-circumferentially-spaced longitudinal channels extend from the inner end of the distal portion to the outer end of the proximal portion. The depth of these longitudinal channels is substantially constant as they extend from the inner end of the distal portion to the inner end of the proximal portion. Thereafter, however, the depth of these channels gradually decreases as the channels extend from the inner end of the proximal portion to the outer end of the proximal portion. Each of the longitudinal channels also has an associated bore communicating therewith. Each of these bores extends from the inner end of the distal portion (where it communicates with its associated longitudinal channel) toward the outer end of the distal portion.

The at least two barbs extend in equally-circumferentially-spaced relation to each other, and in equally spaced radial relation to the longitudinal axis, with one end of each barb being disposed in a bore and the other end of the barb being substantially radially displaced from the body, whereby each barb will be aligned with and extend out of one longitudinal channel. Each barb is curved in its normal unstressed state, but is capable of being elastically deformed to a substantially straight configuration.

The attachment means are formed in the proximal portion of the body. In a preferred embodiment, the attachment means comprise a round or elongated hole extending diametrically through the proximal portion of the body, adjacent its outer end and through the regions of the proximal portion which are located between the longitudinal channels.

The foregoing anchor is intended to be used in conjunction with a novel installation tool which generally includes an elongated shaft having a distal end and a proximal end. Tubular means, associated with the distal end of the shaft, are adapted to receive and hold the middle and proximal portions of the anchor's body. Plunger means are provided for engagement with the outer end of the proximal portion of the anchor, with the plunger means being adapted to extend axially through the tubular means so as to be able to separate an anchor from the tubular means on command.

In one preferred embodiment of the installation tool, adapted for use with an anchor of the type described above having two barbs, the installation tool's elongated shaft is formed hollow so as to provide the tubular means integral with the distal end of the shaft, and includes four equally-circumferentially-spaced longitudinal slots extending proximally from the shaft's distal end. A first two of these slots are diametrically opposed to one another and have a first longitudinal length. These first two longitudinal slots are adapted to accommodate the two barbs of a suture anchor received by the installation tool's hollow shaft. The second two of the longitudinal slots are diametrically opposed to each other and have a second longitudinal length which is longer than the first longitudinal length. The second two slots are adapted to accommodate the two lengths of suture extending out of the anchor's suture-receiving hole. The length of the shaft's two barb-receiving slots and the length of the shaft's two suture-receiving slots are related to one another and to the dimensions of the suture anchor so that when a suture anchor has its middle and proximal portions disposed in the shaft's hollow distal end, the anchor's barbs will engage the proximal ends of the barb-receiving slots but the anchor's suture need not engage the proximal end of shaft's suture-receiving slots. In this first preferred embodiment of the installation tool, the plunger means comprises an elongated solid rod adapted for telescopic insertion through the central lumen of the hollow shaft. Preferably the distal end of the plunger rod has a reduced diameter relative to the remainder of the plunger rod. For convenience, handle portions may be disposed about the proximal ends of both the hollow shaft and the solid rod. The preferred material for the components of this tool is stainless steel.

In a second preferred embodiment of the installation tool, again adapted for use with an anchor of the type described above and having two barbs, the installation tool's elongated shaft is solid and preferably formed of stainless steel. It comprises a distal portion having a first relatively small diameter, an intermediate portion having a second relatively intermediate diameter, and a proximal portion having a third relatively large diameter. A first shoulder is formed where the distal portion meets the intermediate portion, and a second shoulder is formed where the intermediate portion meets the proximal portion. A shallow circumferential groove is formed in the intermediate portion, intermediate the first shoulder and the second shoulder.

The installation tool also comprises tubular means in the form of a tubular sleeve having a distal end and a proximal end, a central bore, and preferably formed out of plastic. The tubular sleeve preferably has an outer diameter approximately equal to the diameter of the shaft's proximal portion, and an inner diameter approximately equal to the diameter of the shaft's intermediate portion and somewhat less than the diameter of the suture anchor's body. A counterbore is formed in the distal end of the tubular sleeve, with a shoulder being created at the junction of the sleeve's bore and counterbore. This counterbore has an inner diameter slightly larger than the diameter of the suture anchor's body, so that a suture anchor may be inserted into the distal end of the sleeve and engage the shoulder. The sleeve also has an interior rib which is positioned adjacent the proximal end of the sleeve. The rib is sized so as to make a sliding frictional engagement with the intermediate portion of the shaft, and to make a catching engagement with the shaft's circumferential groove. The length of the sleeve is less than the combined length of the shaft's distal portion and intermediate portion. Four equally-circumferentially-spaced, equally-sized longitudinal slots are formed in the distal end of the sleeve to accommodate the two barbs and two suture lengths of a suture anchor when the suture anchor has its proximal and intermediate portions disposed in the interior of the hollow sleeve. The various members of the system are sized so that when the sleeve is positioned so that its rib is disposed in the shaft's circumferential groove, and when a suture anchor is disposed in the hollow sleeve so that the proximal end of the suture anchor's body engages the sleeve's internal shoulder, the outer end of the anchor's proximal portion will be spaced from the shaft's distal portion and the suture anchor's barbs and suture length will be spaced from the proximal ends of the sleeve's longitudinal slots. At the same time, the various members of the system are sized so that when the sleeve is positioned so that its proximal end engages the shaft's second shoulder, the distal portion of the shaft will project out of the distal end of the sleeve.

The method of using the present system to deploy an anchor in a hole in a workpiece includes the steps of: (1) providing the system components; (2) forming a hole of the desired size in the workpiece; (3) attaching an object (e.g. a suture) to the anchor's attachment means; (4) inserting the distal and middle portions of the anchor's coupling member into the distal end of the tool's tubular means so that the barbs and suture lengths project radially outwardly from the longitudinal slots formed therein; (5) manipulating the installation tool so that the distal portion of the anchor enters the proximal end of the hole in the workpiece and the distal end of the tubular means engages the surface of the workpiece adjacent the periphery of the hole; (6) driving the anchor into the hole by forcing the plunger means to move through and beyond the tubular means; and (7) withdrawing the plunger means from the hole and removing the distal end of the tubular means from its engagement with the workpiece surface adjacent the hole.

BRIEF DESCRIPTION OF THE DRAWINGS

These and other objects, features and advantages of the present invention will be more fully disclosed in, or rendered obvious by, the following detailed description of the preferred embodiments of the invention, which are to be considered together with the accompanying drawings wherein like numbers refer to like parts and further wherein.

DETAILED DESCRIPTION OF THE PREFERRED EMBODIMENTS

Figure 1:
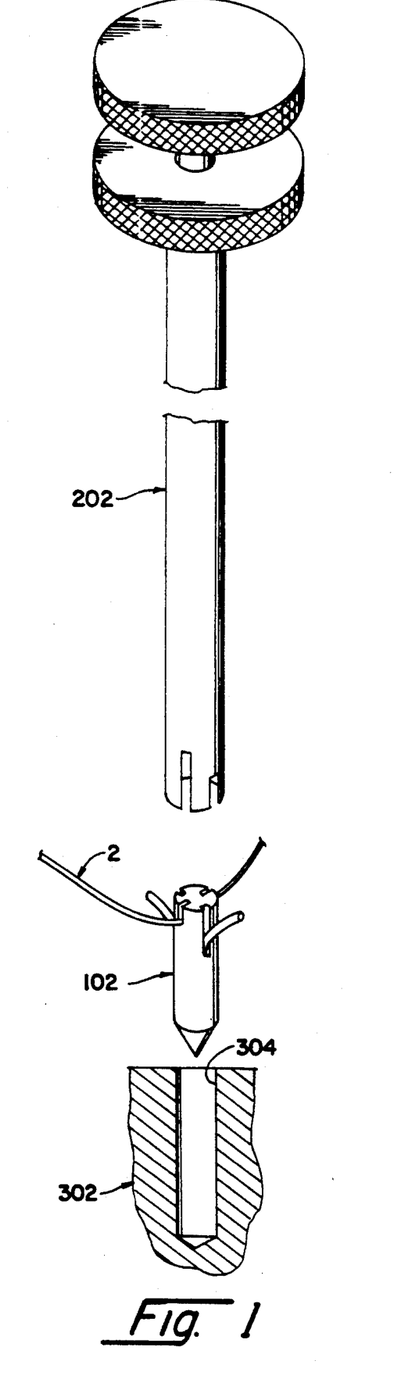
FIG. 1 is a schematic perspective view showing a suture, a suture anchor, a suture anchor installation tool, and a target bone, all in exploded relation to one another.

Referring now to the drawings, and particularly to FIG. 1, there is shown a suture 2, a suture anchor 102, a suture anchor installation tool 202 and a target bone 302 having a hole 304 formed therein. Suture 2 is attached to anchor 102 as will hereafter be described in detail, and installation tool 202 is adapted to install anchor 102 in the hole 304 formed in target bone 302 as will also hereinafter be described in detail.

Turning now to FIGS. 1, 2, 2A and 2B, anchor 102 generally comprises a body 104 having a longitudinal axis 106, and at least two identical barbs 108. Specifically, body 104 has a distal portion 110 having an inner end 112 and an outer end 114, a proximal portion 116 having an inner end 118 and an outer end 120, and a middle portion 122 connecting the inner end 112 of distal portion 110 to inner end 118 of proximal portion 116. Body 104 has a maximum cross-section (taken transverse to the longitudinal axis 106) which is only slightly smaller than the diameter of hole 304 in target bone 302, as will hereinafter be seen in greater detail. Body 104 is preferably formed out of 6AL-4V ELI titanium.

Figure 2:
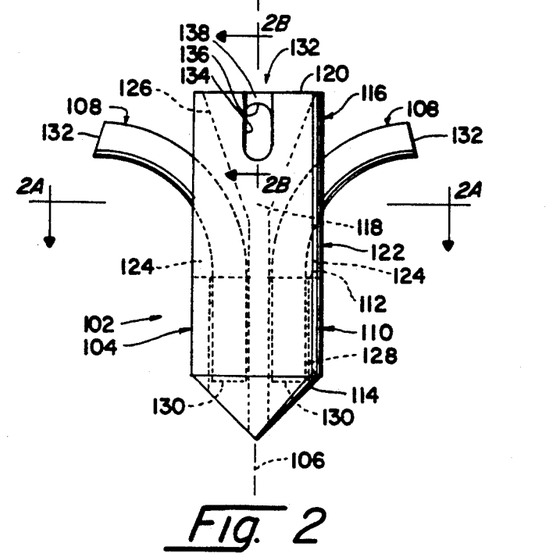
FIG. 2 is a side elevational view of the suture anchor shown in FIG. 1.
Figure 2A:
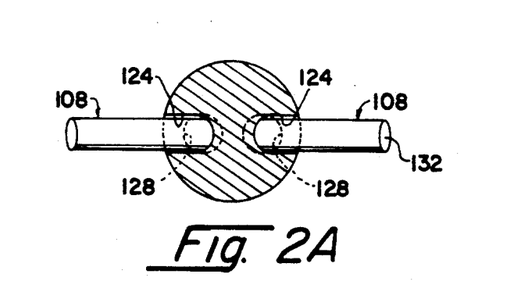
FIG. 2A is a cross-sectional view of the same suture anchor, taken along line 2A—2A of FIG. 2.
Figure 2B:
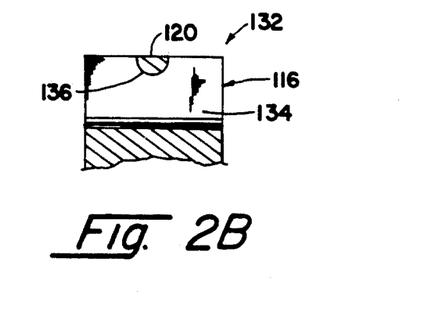
FIG. 2B is a cross-sectional view of the same suture anchor, taken along line 2B—2B of FIG. 2.

At least two equally-circumferentially-spaced longitudinal channels 124 are formed in the exterior of body 104. Each of the longitudinal channels 124 extends from inner end 112 of distal portion 110 to outer end 120 of proximal portion 116. In the anchor embodiment shown the drawings, there are two such channels 124, each having a width of approximately 0.022 inches and a depth (as measured in middle portion 122) of approximately 0.028 inches. In fact, there are always exactly as many channels 124 as there are barbs 108 on the anchor. Thus, in the embodiment shown in the drawings, inasmuch as there are two barbs 108 on body 104, there are two channels 124. The interior bases 126 of channels 124 extend substantially parallel to longitudinal axis 106 from first end 112 of distal portion 110 to inner end 118 of proximal portion 116. From inner end 118 of proximal portion 116 to outer end 120 of proximal portion 116, bases 126 of channels 124 slant outwardly relative to the anchor's longitudinal axis 106 at an angle of between about 12 and 30 degrees. Longitudinal channels 124 extend all the way to, and open on, outer end 120 of proximal portion 116.

For purposes of definition, middle portion 122 can be considered to end, and proximal portion 116 can be considered to start, at the point at which bases 126 of channels 124 begin to incline outwardly.

At least two longitudinal bores 128 extend into inner end 112 of distal portion 110, parallel to longitudinal axis 106 and adjacent to bases 126 of each of the channels 124. In the embodiment shown, there are two such bores 128. In fact, there are always exactly as many of these bores 128 as there are barbs 108 on the anchor, and hence exactly as many of these bores 128 as there are channels 124. One bore 128 communicates with each channel 124, so as to form an extension of that channel.

Representative dimensions for body 104 may be as follows: the diameter of the body is approximately 0.066 inches; the longitudinal length of distal portion 110 is about 0.078 inches; the longitudinal length of middle portion 122 is approximately 0.022 inches; and the longitudinal length of proximal portion 116 is approximately 0.112 inches. The diameters of bores 128 are approximately 0.022 inches, and they may extend from first end 112 of distal portion 110 all the way through that distal portion to open on its outer end 114. Of course, bores 128 may also extend only part of the way through distal portion 110 and thus terminate short of outer end 114, without departure from the present invention.

Barbs 108 are each formed from a curved length of wire having a first or inner end 130 and a second or outer end 132. Barbs 108 are formed out of a relatively strong, highly elastic material such as a titanium alloy. Such materials are readily available from Raychem Corporation of Menlo Park, California and Shape Memory Applications, Inc. of Sunnyvale, Cal., among others. The first or inner ends 130 of barbs 108 are attached to the anchor's distal portion 110 so that they extend axially and radially outward therefrom. In a preferred embodiment, barbs 108 have a diameter of approximately 0.020 inches, and in their unrestrained state define an arc of approximately 90 degrees of loop, approximately 0.202 inches in diameter (when measured to the inside edge of the loop). Each barb 108 is capable of being elastically deformed to a substantially straight configuration when desired.

The length of barbs 108 is preferably slightly greater than or equal to the longitudinal length of anchor body 104, as measured from the distal-most tip of outer end 114 of distal portion 110 to outer end 120 of proximal portion 116. The barbs may be made integrally with anchor body 104. In the preferred embodiments, however, the first or inner ends 130 of curved barbs 108 are inserted into the straight bores 128 so that the barbs extend substantially all the way to outer end 114 of distal portion 110. The tendency of the curved barbs 108 to return to their natural configuration after insertion into the straight bores 128 acts to securely hold the barbs in position within bores 128. The permanence of this engagement may be further assured by crimping distal portion 110 inwardly adjacent bores 128, or otherwise mechanically locking in place the portions of barbs 108 inserted into bores 128.

In view of the foregoing construction, it will be seen that barbs 108 will normally project axially rearward from the anchor's inner end portion 112 and radially outward from the circumferential outer surfaces of body 104, but they may also be bent inwardly under sufficient forces so that they can lie against floors 126 of channels 124.

In this respect it is to be appreciated that barbs 108 and channels 124 are also sized and positioned relative to one another so that when barbs 108 are forced inwardly so as to lie against channel floors 126, all but the outermost portions 132 of barbs 108 will reside inside channels 124. Due to the inclined geometry of floors 126 at the proximal end of body 104, however, the outermost portions 132 of barbs 108 will remain at least slightly outboard of anchor body 104 even when barbs 108 lie against channel floors 126.

Suture attachment means 132 are provided at proximal portion 116 of the anchor body. In the embodiments shown, suture attachment means 132 comprises a bore 134 which extends through body 104, transverse to longitudinally axis 106 and between the slanted bases 126 of channels 124, and adjacent the outer end 120 of proximal portion 116. The portion of bore 134 closest to outer end 120 of proximal portion 116 forms a smoothly contoured bearing surface 136 such that no sharp edges will be presented to a length of suture threaded through bore 134 and engaging surface 136, and such that a length of suture threaded through bore 134 and engaging surface 136 may be slid along that bearing surface 136 if desired after anchor 102 has been deployed in bone hole 304. In addition, indented portions 138 preferably connect the proximal end of bore 134 to the outer end 120 of proximal portion 116, thereby providing a protected pathway for the suture to emerge from bore 134 and extend proximally of the suture anchor.

It will be appreciated that by placing attachment means 132 at the proximal end of anchor 102 and locating attachment means 132 on the longitudinal axis of the anchor, any forces applied to the free ends of the suture once the suture anchor has been set in bone will not tend to induce rotational torque upon the anchor.

It is also to be appreciated that by inclining floors 126 of channels 124 at the proximal end of anchor body 104, sufficient body material will be provided about bore 134 so as to ensure the structural integrity of the suture attachment means 132, while still allowing anchor 102 to be formed with the narrowest possible body diameter.

Several different insertion tools may be used to deploy anchor 102. In general, these installation tools comprise an elongated shaft having a distal end and a proximal end. Tubular means, associated with the shaft's distal end, are provided to receive and hold the middle and proximal portions 122 and 116 of anchor 102. Plunger means are also provided for ejecting anchor 102 from the tubular means. One such installation tool is shown in FIGS. 3, 3A and 4A–4C; another such installation tool is shown in FIGS. 5, 5A, 5B and 6A–6C. Each of these two installation tools will now be separately described.

Looking first at the installation tool 202 disclosed in FIGS. 3, 3A and 4A-4C, this tool comprises an elongated, hollow shaft 204 having a distal end 206 and a proximal end 208. An axial bore 210 extends through shaft 204 and has a cross-section, taken transverse to the longitudinal axis 212 of the shaft, corresponding to, but slightly larger than, the transverse cross-section of body 104 of anchor 102. A plurality of circumferentially spaced, longitudinally extending slots 214, 216, 218 and 220 extend proximally from distal end 206 of shaft 204, through the side wall 222 of the shaft. The purpose of these slots is to accommodate the barbs 108 and suture 2 which extend outwardly from body 104 of anchor 102 when the anchor is mounted partially within the distal portion 206 of shaft 204, as will hereinafter be described in further detail. Accordingly, in the embodiment shown, diametrically opposed slots 216 and 220 are provided to receive barbs 108, and diametrically opposed slots 214 and 218 are provided to receive the portions of the suture 2 extending outwardly from either end of the anchor's suture bore 134. The lengths of longitudinal slots 216 and 220 are related to the lengths of longitudinal slots 214 and 218 so that when a suture anchor 102 is disposed in the distal end of shaft 204, i.e., so that the suture anchor's middle and proximal portions 122 and 116 are positioned in the shaft's hollow interior, the anchor's barbs 108 will engage the proximal ends of the shaft's barb-receiving slots 216 and 220, while the anchor's suture 2 need not engage the proximal ends of the shaft's suture-receiving slots 214 and 218. Of course, it will also be understood that the number and arrangement of the slots 214, 216, 218 and 220 may be varied according to the specific configuration of the anchor 102, i.e., if there are more than two barbs 108, there will be more than two slots 216, 220 to accommodate those barbs, and if the object (e.g. suture) attached to the attachment means 132 requires it, the size and number of slots 214 and 218 may be adjusted accordingly.

Figures 3, 3A:
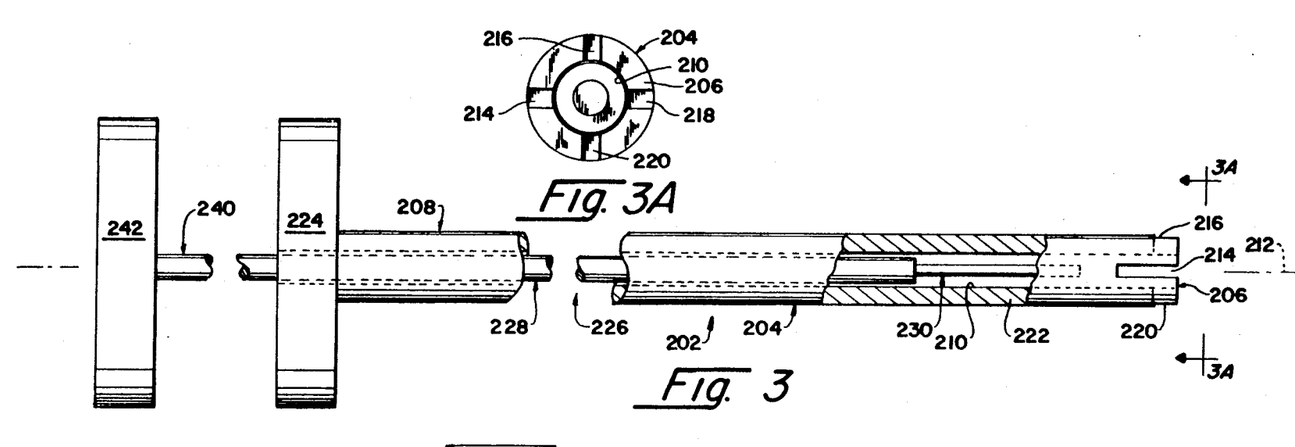
FIG. 3 is a side elevational view in partial section of the suture anchor installation tool shown in FIG. 1.
FIG. 3A is a bottom plan view of the same installation tool, taken along line 3A—3A of FIG. 3.

Shaft 204 is provided with a handle 224 at the proximal end of the shaft in order to facilitate the manipulation of tool 202.

Tool 202 also comprises a plunger 226. Plunger 226 includes a solid rod 228 having a distal end 230 and a proximal end 240. Rod 228 is sized for telescopic insertion into and through bore 210 of hollow shaft 204. Rod 228 is longer than hollow shaft 204, and also includes a handle 242 at the proximal end of the rod. In the embodiment shown, handles 224 and 242 are designed to matingly engage one another when plunger rod 228 is fully inserted through bore 210 of hollow shaft 204. It is to be appreciated that when handles 224 and 242 so engage one another, the distal end 230 of plunger rod 228 will protrude from the distal end 206 of hollow shaft 204. In fact, the elements of installation tool 202 are sized so that when handles 224 and 242 engage one another, the distal end of rod 228 will protrude from the distal end of hollow shaft 204 by exactly the same distance that the suture anchor 102 is to be set into target bone 302.

Furthermore, the proximal end 240 of rod 228 is preferably sized so as to form a close sliding fit with bore 210. This construction will help ensure the continued axial alignment of rod 228 when it is delivering deployment forces to the suture anchor. In fact, the fit between the proximal end 240 of rod 228 and bore 210 of shaft 204 is preferably sufficiently tight so as to ensure that only deliberate motion of rod 228 will take place, while at the same time the fit is not so tight as to impede such motion. The distal portion 230 of rod 228 is of a reduced diameter relative to the proximal portion 240. In fact, distal portion 230 has a diameter less than the diameter of suture anchor body 104, whereas proximal portion 240 has a diameter approximately equal to the diameter of suture anchor body 104. The benefit of providing such a reduced diameter distal portion 230 will become readily apparent in connection with the use of the present invention, as set forth in detail below.

Representative dimensions for an installation tool of the type just described may be stated as follows:

| Hollow shaft 204: | |
|---|---|
| Length | 3.75 inches |
| Outer diameter | 0.195 inches |
| Inner diameter | 0.070 inches |
| Width of slots | 0.024 inches |
| Length of slots 214 and 218 | 0.132 inches |
| Length of slots 216 and 220 | 0.055 inches |
| Handle thickness | 0.195 inches |
| Handle diameter | 0.750 inches |
| Plunger rod 228: | |
| Handle thickness | 0.195 inches |
| Handle diameter | 0.750 inches |
| Length of rod 228 | 4.195 inches |
| Diameter of proximal portion 240 | 0.068 inches |
| Length of distal portion 230 | 0.250 inches |
| Diameter of distal portion 230 | 0.032 inches |

Figure 4A:
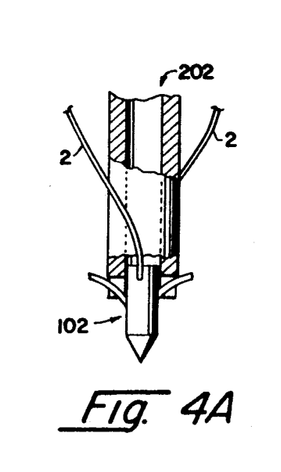
FIG. 4A is a partial side elevational view of the suture, suture anchor and installation tool of FIG. 1 assembled together in preparation for inserting the anchor into the hole in the target bone.
Figure 4B:
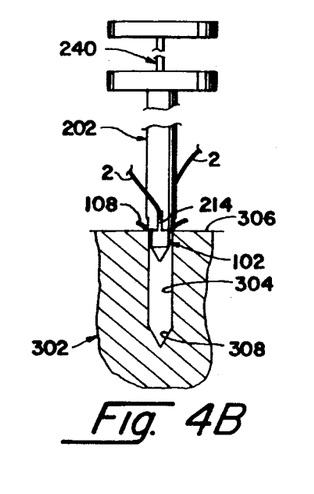
FIG. 4B is a partial side elevational view of the assembly of FIG. 4A positioned adjacent the target bone.
Figure 4C:
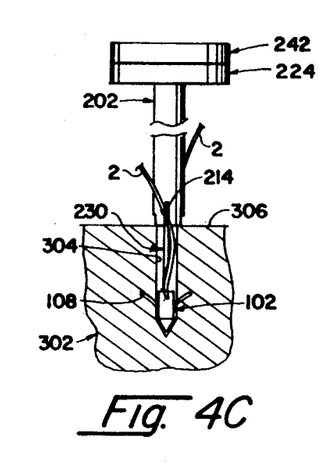
FIG. 4C is a partial side elevational view of the assembly of FIG. 4B inserting the suture anchor into the target bone, with the suture being cut away immediately adjacent the anchor's attachment means so as to provide a superior view of the installation tool.

Looking next at FIGS. 4A, 4B and 4C, anchor 102 and installation tool 202 are intended to be used as follows to attach a suture 2 to a bone 302. First, the suture 2 is attached to the suture anchor's attachment means 132 by threading the suture through hole 134, with both ends of suture 2 remaining free. Thereafter, anchor 102 is attached to distal end 206 of the installation tool's hollow shaft 204. This attachment is accomplished by first removing plunger 226 from hollow shaft 204; next aligning the longitudinal axis 106 of anchor body 104 with the longitudinal axis 212 of hollow shaft 204, and aligning suture 2 (extending through anchor bore 134) with the longer slots 214,218 at the distal end of hollow shaft 204 and aligning anchor barbs 108 with the shorter slots 216,220 at the distal end of hollow shaft 204; and then sliding the proximal and middle portions 116 and 122 of the anchor body into distal end 206 of hollow shaft 204 until barbs 108 engage the proximal ends of the shorter slots 216,220. It will be appreciated that due to the sizing of the system components, the suture 2 which is threaded through anchor bore 134 need not engage the proximal ends of the longer slots 214, 218 when barbs 108 engage the proximal ends of shorter slots 216, 220. See FIG. 4A.

Thereafter, the free ends of suture 2 are pulled towards handles 224,242 so as to keep the suture's length under control and so as to help keep suture anchor 102 mounted in the distal end of shaft 204. Then plunger 226 is loaded into hollow shaft 204 so that the plunger's leading tip 230 approaches or even lightly contacts the outer end 120 of anchor 102. Next, tool 202 is manipulated so as to bring the distal portion 110 of anchor 102 into the top of the hole 304 formed in workpiece 302. See FIG. 4B. As noted above, the cross-section of the anchor's body 104 will be only slightly smaller than the diameter of hole 304. Accordingly, in this position the distal end 206 of hollow shaft 204 will bear against the workpiece's top surface 306 which surrounds the anchor-receiving hole 304.

From this position, anchor 102 may be driven into hole 304 so as to achieve its desired anchoring location within the bone. This is accomplished by driving plunger handle 242 downward until it engages shaft handle 224. This causes the distal end 230 of plunger 226 to engage the outer end 120 of anchor 102 with the axial driving force needed to move the suture anchor out of shaft 204 and down into bone hole 304 so as to seat itself at the bottom end 308 of the bone hole. See FIG. 4C. As this deployment occurs, the suture anchor's barbs 108 engage the portions of bone 302 which define hole 304 and, due to this engagement, are folded back into channels 124 to the extent required to permit the anchor to pass down the bone hole. At the same time, the resilient nature of barbs 108 causes them to constantly exert an outward force against the surrounding bone, so that the suture anchor will be locked against retreat back out of the hole. The proximal ends of suture 2 are then released and tool 202 is withdrawn from the workpiece, leaving anchor 102 emplaced in bone 302 and the suture lengths emanating therefrom.

It is to be appreciated that only the reduced diameter distal portion 230 of plunger 226 actually passes down into bone hole 304. The larger diameter proximal portion 240 of plunger 226 and, even more importantly, the engaging and supporting distal end 206 of hollow shaft 204 remaining outside the bone hole at all times during anchor deployment. Since the distal portion 230 of the plunger is sized so as to be smaller than the diameter of anchor body 104, it will be appreciated that bone hole 304 can be sized according to the dimensions of the bone anchor being used, and need not be formed large enough to accommodate the anchor engaging and supporting portion of the installation tool. This feature is a major advantage over prior art installation tools.

Furthermore, the reduced diameter of the plunger's distal end 230 provides an enlarged passageway for the suture between the walls of the bone hole and the plunger body. This passageway reduces the possibility of damage to the suture during the installation procedure due to its possible entrapment between the installation tool and/or the anchor body and the sides of the bone hole.

It has been found that, in forming bone hole 304, it is desirable to form a hole with a generally conical geometry at its bottom end 308. This conical geometry generally matches the configuration of the anchor's outer end 114, so that the anchor seats itself more effectively in bone hole 304.

An alternative form of installation tool is shown in FIGS. 5, 5A, 5B and 6A–6C. More specifically, an installation tool 402 is disclosed which includes an elongated metal (preferably stainless steel) shaft 404 and a tubular sleeve 406, preferably formed from a polymeric, bio-compatible, plastic material.

Figures 5, 5A, 5B, 7, 7A:
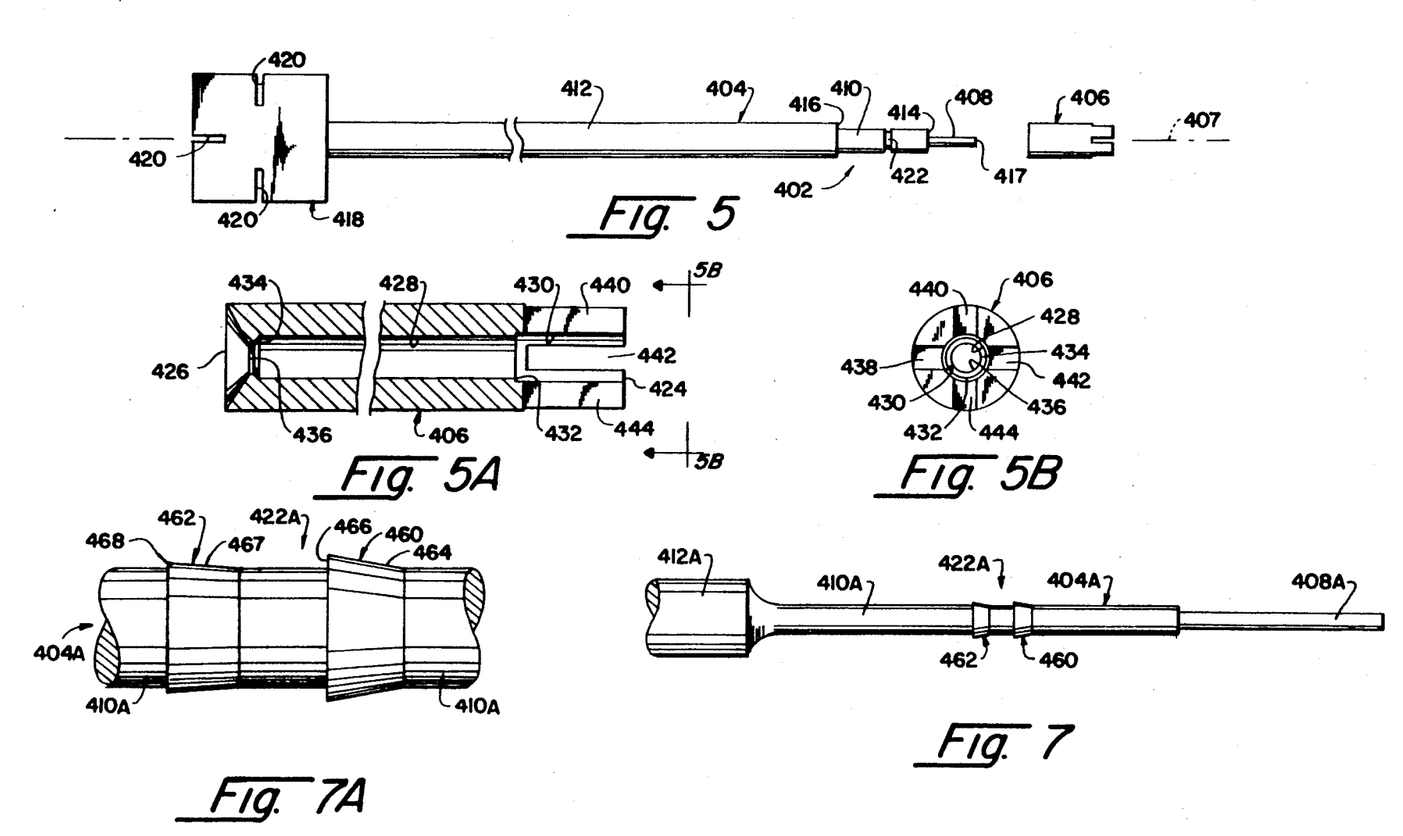
FIG. 5 is an exploded side elevational view of an alternative form of installation tool formed in accordance with the present invention.
FIG. 5A is an enlarged side elevational view in section showing the tubular sleeve member of the installation tool of FIG. 5.
FIG. 5B is a bottom plan view of the same tubular sleeve member, as taken along line 5B—5B of FIG. 5A.
FIG. 7 is a partial side elevational view showing an alternative form of elongated shaft which may be used in forming an installation tool of the sort shown in FIG. 5.
FIG. 7A is an enlarged partial side elevational view showing selected details of the elongated shaft shown in FIG. 7.

Shaft 404 comprises a distal end portion 408 having a first relatively small diameter, an intermediate portion 410 having a second relatively intermediate diameter, and a proximal end portion 412 having a third relatively large diameter. A first shoulder 414 is formed where distal portion 408 meets intermediate portion 410, and a second shoulder 416 is formed where intermediate portion 410 meets proximal portion 412. Shaft 404 terminates in a distal end surface 417. A handle 418 is attached to shaft 404 adjacent its proximal end 412. Handle 418 may be similar to the handles 224 and 242 discussed above or, alternatively, handle 418 may be generally rectangular in shape and include suture receiving slots 420 adapted to hold, through frictional engagement, a suture extending from a suture anchor mounted to tool 402.

A circumferential groove 422 is formed in the outer surface of intermediate portion 410 approximately midway along its length. In the drawings, groove 422 extends all the way around the circumference of intermediate portion 410, however, groove 422 may also be formed as a series of separate, circumferentially-extending groove arcs separated by lands, or as a series of discrete, circumferentially spaced indentations, if desired.

Tubular sleeve 406 has a distal end 424, a proximal end 426, and an outer diameter substantially equal to the diameter of the shaft's proximal portion 412. A central bore 428 passes through sleeve 406. A counterbore 430 is formed at the distal end of sleeve 406. Counterbore 430 intersects bore 428 at a shoulder 432. A rib 434 extends radially into bore 428 adjacent the proximal end of the sleeve. Rib 434 defines a diametrical opening 436 which is smaller than the internal diameter of bore 428. In the event that shaft groove 422 is broken up into discrete arcs or indentations, rib 434 is correspondingly broken.

A plurality of circumferentially spaced, longitudinally extending slots 438, 440, 442 and 444 extend through the side wall of sleeve 406, opening on distal end 424 and extending proximally therefrom. The purpose of these slots is to accommodate the barbs 108 and suture 2 which extend outwardly from the body of an anchor 102 when the anchor is mounted partially within tubular sleeve 406, as will hereinafter be described in further detail. Accordingly, in the embodiment shown, slots 440 and 444 are provided to receive the anchor's barbs 108, and slots 438 and 442 are provided to receive the portions of suture 2 extending outwardly from either end of anchor bore 134. It will, of course, also be understood that the number and arrangement of the slots 438, 440, 442 and 444 may be varied according to the specific configuration of the anchor 102, i.e., if there are more than two barbs on the anchor, more slots 440, 444 will be provided to accommodate those barbs, and if the object attached to the anchor's attachment means requires it, the size and number of slots 438, 442 will be adjusted to accommodate the portions of the object attached to the attachment means.

Tubular sleeve 406 is sized so that its central bore 428 has an inside diameter just slightly larger than the outside diameter of the shaft's intermediate portion 410, but smaller than the outside diameter of the suture anchor's body 104; its counterbore 430 has an inside diameter just slightly larger than the outside diameter of the suture anchor's body 104; and its rib 434 has a diametrical opening 436 slightly less than the outside diameter of the shaft's intermediate portion 410 but slightly larger than the circle enscribing the floor of shaft groove 422.

In view of this construction, sleeve 406 may be telescoped onto the shaft's intermediate portion 410 so that the sleeve's rib 434 makes a tight sliding fit with the outside diameter of the shaft's intermediate portion 410, with the sleeve being movable between first and second operative positions. In the first of these positions, i.e., that shown in FIG. 6A, rib 434 resides in the shaft's groove 422 so as to yieldably lock sleeve 406 to shaft 404. In the second of these positions, i.e., that shown in FIG. 6C, the proximal end 426 of the sleeve 406 engages the shoulder 416 formed at the intersection of intermediate portion 410 and proximal portion 412. Shaft 404 and sleeve 406 are sized so that when sleeve 406 is disposed in its first position so that its rib 434 resides in shaft groove 422, the distal end surface 417 of shaft 404 will terminate short of sleeve shoulder 432 (FIG. 6A), but when sleeve 406 is disposed in its second position so that its proximal end 426 engages shaft shoulder 416, distal end surface 417 of shaft 404 will project outward from the distal end of sleeve 406 (FIG. 6C).

It is also to be appreciated that shaft 404 and tubular sleeve 406 are sized relative to one another so that sleeve 406 can rotate circumferentially about shaft 404 when sleeve 406 is in either of its first and second operative positions, or at any position therebetween.

Figure 6A:
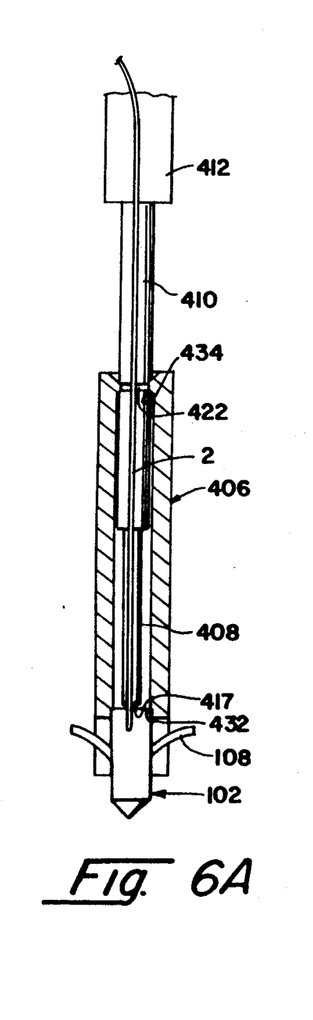
FIG. 6A is a side elevational view of the suture, suture anchor and installation tool of FIG. 5 assembled together in preparation for inserting the anchor into the hole in the target bone.
Figure 6B:
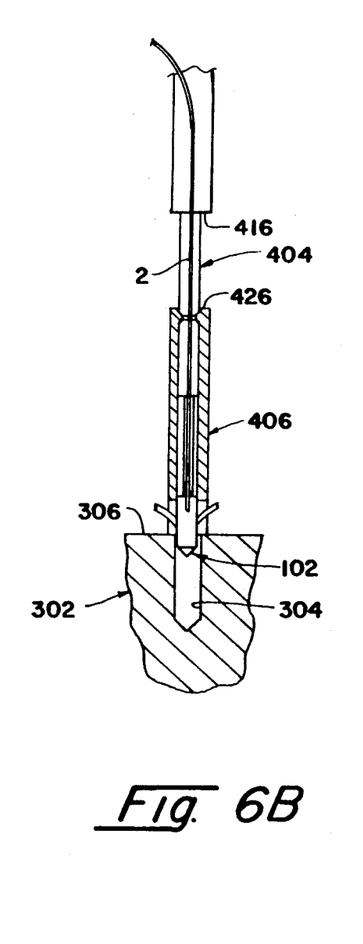
FIG. 6B is a partial side elevational view of the assembly of FIG. 6A positioned adjacent the target bone.
Figure 6C:
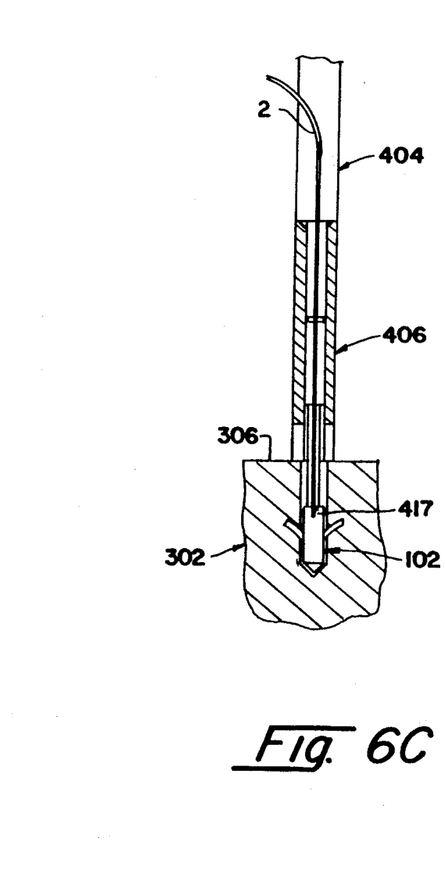
FIG. 6C is a partial side elevational view of the assembly of FIG. 6B inserting the suture anchor into the target bone.

It is to be appreciated that when sleeve 406 is in the position shown in FIG. 6A, i.e., so that sleeve rib 434 is disposed in shaft groove 422, an anchor 102 may be disposed in sleeve 406 so that the proximal end 120 of the anchor engages and is stopped by sleeve shoulder 432 and the distal end of anchor 102 projects outward from the distal end of sleeve 406. Sleeve slots 438, 440, 442 and 444 are sized sufficiently long that when an anchor 102 is disposed in sleeve 406 and has its distal end 120 engaging sleeve shoulder 432, anchor barbs 108 and suture 2 need not engage the proximal ends of slots 438, 440, 442 and 444.

Representative dimensions for tool 402 may be stated as follows:

| | |
|---|---|
| Overall length of shaft 404: | 3.05 inches |
| Proximal Portion 412 | 2.20 inches |
| Intermediate Portion 410 | 0.55 inches |
| Distal Portion 408 | 0.30 inches |
| Shaft Diameters: | |
| Proximal Portion 412 | 0.125 inches |
| Intermediate Portion 410 | 0.060 inches |
| Distal Portion 408 | 0.038 inches |
| Width of Groove 422 | 0.020 inches |
| Tubular Sleeve 406: | |
| Inner Diameter (bore 428) | 0.062 inches |
| Outer Diameter | 0.125 inches |
| Length (overall) | 0.700 inches |
| Rib Width (opening 436) | 0.020 inches |
| Rib Thickness (longitudinal length) | 0.0025 inches |
| Width of slots 438, 440, 442, 444 | 0.024 inches |
| Length of slots 438, 440, 442, 444 | 0.132 inches |

Installation tool 402 is used as follows.

First, the tool has its sleeve 406 placed in its aforementioned first position, i.e., so that it is in the position shown in FIG. 6A wherein the sleeve's rib 434 is positioned in the shaft's groove 422. Then a suture anchor 102 is loaded into the distal end of tubular sleeve 406 so that the distal end 120 of the anchor engages sleeve shoulder 432, and so that anchor barbs 108 reside in two diametrically opposed sleeve slots (e.g. sleeve slots 440, 444) and the suture lengths emanating from the anchor reside in the remaining two diametrically opposed sleeve slots (e.g. sleeve slots 438, 442), with barbs 108 and the suture lengths not necessarily engaging the proximal ends of slots 438, 440, 442 and 444. It will be appreciated that when the system components are in the foregoing positions, the shaft's distal end surface 417 will terminate short of the anchor's proximal end surface 120, and the distal portion of anchor 102 will extend out of the distal end of tool 402. See FIG. 6A. Preferably the free ends of the suture are wrapped into handle slots 420 under slight tension so as to keep the suture ends under control and so as to help hold suture anchor 102 to the distal end of tubular member 406.

Next, tool 402 is manipulated so as to bring the distal portion 110 of anchor body 104 into the top of the hole 304 formed in workpiece 302. As noted above, the cross-section of the anchor's body 104 will be only slightly smaller than the diameter of hole 304. Accordingly, in this position the distal end 424 of tubular sleeve 406 will bear against the workpiece's top surface 306 which surrounds the anchor-receiving hole 304. See FIG. 6B.

From this position anchor 102 may be driven into hole 304 so as to achieve its desired anchoring location within the bone. This is accomplished by driving shaft handle 418 downward, until shaft groove 422 moves past sleeve rib 434. Shaft 404 continues moving downward until shoulder 416 of shaft 404 engages the sleeve's proximal end 426. This action causes the distal end surface 417 of shaft 404 to engage the proximal end 120 of anchor 102 and drive it downward into bone hole 304. See FIG. 6C. As this deployment action occurs, the suture anchor's barbs 108 engage the portions of bone 302 which define hole 304 and, due to this engagement, are forced inwardly into anchor channels 124 to the extent required to permit the suture anchor to pass down the bone hole. At the same time, of course, the resilient nature of barbs 108 causes them to springly engage the surrounding bone and thereby cause the suture anchor to be locked to the interior of the bone. Then the proximal ends of suture 2 are released from tool handle 418 and tool 402 is withdrawn from the workpiece, leaving anchor 102 emplaced in bone 302 and the suture lengths emanating therefrom.

It is to be appreciated that with the installation tool of FIGS. 5, 5A, 5B and 6A-6C, only the reduced diameter distal portion 408 of the shaft actually enters the bone hole. The larger diameter intermediate portion 410 and, even more importantly, the anchor engaging and supporting distal end 424 of hollow sleeve 406 remain outside the bone hole at all times. Thus it will be appreciated that bone hole 304 can be sized according to the dimensions of the bone anchor being used, and need not be formed large enough to accommodate the anchor engaging and supporting portion of the installation tool as well. As with installation tool 202 described above, this is a major advance over prior art installation tools.

It is also to be appreciated that inasmuch as tubular sleeve 406 is free to rotate circumferentially about shaft 404 when it is in either of its first and second positions, or at any position therebetween, rotational torque imparted to shaft 404 during insertion will not tend to be imparted to the anchor 102. This is because any rotational torque imparted to handle 418 during insertion will tend to be isolated from anchor 102 by the rotatable nature of sleeve 406. Thus, any inadvertent rotation of handle 418 during insertion will not tend to cause undesired damage to bone 302 or anchor 102 during insertion.

Looking next at FIGS. 7 and 7A, there is shown an alternative form of shaft 404A which may be used in place of the shaft 404 which has been disclosed in connection with the installation tool of FIGS. 5, 5A, 5B and 6A-6C. Shaft 404A is identical to shaft 404, except that the groove 422 of shaft 404 has been replaced by generally equivalent rib-engaging means 422A on shaft 404A. More particularly, rib-engaging means 422A comprise a first generally frusto-conical enlargement 460 formed on shaft 410A at the distal side of rib-engaging means 422A, and a second generally frusto-conical enlargement 462 formed on shaft 410A at the proximal side of rib-engaging means 422A. In this shaft embodiment, the diameter of shaft 410A is constant along its length (except for the frusto-conical enlargements 460 and 462) and equal to the diameter of the previous shaft 410. Frusto-conical enlargements 460 and 462 act as a sort of rib-trapping detent along shaft 410A.

More particularly, frusto-conical enlargement 460 comprises a sloping distal surface 464 and a radial stopping surface 466, and frusto-conical enlargement 462 comprises a sloping distal surface 467 and a radial stopping surface 468. Radial stopping surfaces 466 and 468 have a larger outside diameter than rib 434 has in inside opening 436. On account of this construction, it will be seen that a sleeve 406 may be loaded onto shaft 404A by moving the sleeve rearward until its rib 434 engages distal sloping surface 464 and slips past it. At this point the sleeve's rib is releasably captured between the radial stopping surface 466 of the distal frusto-conical enlargement 460 and the sloping distal surface 467 of the proximal frusto-conical enlargement 462, so that the sleeve is releasably captured in its aforementioned first position. This is equivalent to the sleeve's rib being releasably captured in the groove 422 of shaft 404. When the sleeve 406 is to thereafter shift to its aforementioned second position, so that rib 434 leaves rib-engaging means 422A and the sleeve's proximal end 426 engages shaft shoulder 416, rib 434 slips past the inclined surface 467.

By forming the proximal frusto-conical enlargement 462 so that its outside diameter at radial stopping surface 468 is only slightly larger than the diameter of shaft 410A, it will be possible for sleeve 406 to pass from its aforementioned first position to its aforementioned second position with relatively little effort, yet sufficient resistance will still be offered to the passage of sleeve 406 along shaft 404A so as to permit a suture anchor 102 to be conveniently loaded into sleeve 406 and carried by the sleeve prior to deployment. In addition, it will be seen that by forming the proximal frusto-conical enlargement 462 so that its outside diameter is only a little larger than the diameter of shaft 410A, the sleeve's rib 434 can also be moved distally down the shaft past radial stopping surface 468 if desired, albeit with somewhat greater effort than is required to pass rib 434 by inclined surface 467. At the same time, it is preferred to form the distal frusto-conical enlargement 460 so that its outside diameter at radial stopping surface 466 is significantly larger than the diameter of shaft 410A, so that it is relatively difficult for rib 434 of sleeve 406 to move distally down the shaft past radial stopping surface 466. While this construction also tends to make it somewhat more difficult to move sleeve rib 434 past enlargement 460 during assembly of the anchor installation tool, in some circumstances this inconvenience may be acceptable so as to ensure that there is little likelihood that sleeve 406 can become disengaged from shaft 404A during use.

Still other variations, modifications, alterations, changes and the like will occur to those skilled in the art in light of the foregoing description of the preferred embodiments of the invention.

Thus, for example, it will be understood that anchor 2 may be provided with more than two barbs 108, and that installation tools 202 and/or 402 may be modified to accommodate such an anchor configuration. Alternatively, anchor 102 or installation tools 202 or 402 might be formed out of different materials than those specified herein. These and other changes of their type will be obvious to those skilled in the art and are considered to be part of the present invention.

What is claimed is:

1. Apparatus for attaching an object to a workpiece comprising:

an anchor comprising a body and at least two barbs;

said body having a longitudinal axis, a maximum cross-section transverse to said longitudinal axis, a distal portion having an outer end and an inner end, a proximal portion having an outer end and an inner end, and a middle portion joining said inner end of said distal portion and said inner end of said proximal portion;

said middle portion and said proximal portion together defining at least two equally-circumferentially-spaced channels extending inwardly from an axial projection of said maximum transverse cross-section of said distal portion, said channels extending longitudinally from said inner end of said distal portion to said outer end of said proximal portion, each of said channels having a base which is substantially parallel to said longitudinal axis in said middle portion and which slants outwardly relative to said longitudinal axis as it extends from said inner end of said proximal portion to said outer end of said proximal portion, said channels being separated by longitudinal walls extending radially outwardly from said longitudinal axis to an outer surface located on said axial projection of said maximum transverse cross-section;

one of said barbs extending axially and radially outwardly from said inner end of said distal portion adjacent the base of each of said channels to an outer end located radially outwardly of said axial projection of said maximum transverse cross-section, each said barb being curved in its normal, unrestrained state but capable of being deformed into a substantially straight configuration; and attachment means associated with said proximal portion for connecting an object to said anchor.

2. The apparatus of claim 1 wherein said barbs are made of nickel titanium alloy.

3. The apparatus of claim 1 wherein said distal portion of said body defines at least two bores extending longitudinally from said inner end of said distal portion toward said outer end of said distal portion, one bore adjacent said base of each of said channels, and wherein each of said barbs comprises a piece of wire having a first end and a second end, said first end of each said wire fixedly engaging one of said bores in said inner end of said distal portion.

4. The apparatus of claim 1 wherein there are two barbs, and further wherein said attachment means comprises an opening having a second longitudinal axis, said opening extending through said proximal portion and said second longitudinal axis being located in the plane containing said first longitudinal axis.

5. The apparatus of claim 4 wherein said attachment means further includes a cord-like connecting element threaded through said opening so as to securely engage said attachment means and provide at least one free end for attachment to said object.

6. The apparatus of claim 5 wherein said opening is formed in said proximal portion so as to provide a smoothly contoured bearing surface in said proximal portion against which said cord-like element may be slid after said anchor has been deployed in said hole.

7. The apparatus of claim 1 wherein there are three barbs and three channels.

8. The apparatus of claim 1 wherein said anchor is made of a titanium alloy material.

9. The apparatus of claim 1 wherein all of said cross-sections are substantially circular.

10. The apparatus of claim 1 wherein said workpiece is bone.

11. A system for attaching an object to a workpiece using a hole formed in the workpiece, said system comprising:

a) an anchor comprising a body and at least two barbs;

said body having a longitudinal axis, a maximum cross-section transverse to said longitudinal axis slightly smaller than the transverse cross-section of said hole, a distal portion having an outer end and an inner end, a proximal portion having an outer end and an inner end, and a middle portion joining said inner end of said distal portion and said inner end of said proximal portion;

said middle portion and said proximal portion together defining at least two equally-circumferentially-spaced channels extending inwardly from an axial projection of said maximum transverse cross-section of said distal portion, said channels extending longitudinally from said inner end of said distal portion to said outer end of said proximal portion, each of said channels having a base which is substantially parallel to said longitudinal axis in said middle portion and which slants outwardly relative to said longitudinal axis as it extends from said inner end of said proximal portion to said outer end of said proximal portion, said channels being separated by longitudinal walls extending radially outwardly from said longitudinal axis to an outer surface located on said axial projection of said maximum transverse cross-section;

one of said barbs extending axially and radially outwardly from said inner end of said distal portion adjacent the base of each of said channels to an outer end located radially outwardly of said axial projection of said maximum transverse cross-section, each said barb being curved in its normal, unrestrained state but capable of being deformed into a substantially straight configuration; and attachment means associated with said proximal portion for connecting an object to said anchor; and b) an installation tool for deploying said anchor in said hole in said workpiece, said tool comprising:

an elongated shaft having a distal end and a proximal end;

tubular means associated with said distal end of said shaft adapted to receive and hold said middle and proximal portions of said anchor body; and plunger means adapted for engagement with said outer end of said proximal portion of said anchor body, said plunger means being axially movable through said tubular means so as to expell said anchor from said tubular means and to drive said anchor into said hole.

12. The system of claim 11 wherein portions of said object are attached to said attachment means, and further wherein said tool comprises:

an elongated, hollow shaft having a longitudinal axis, an axial bore having a cross-section transverse to said longitudinal axis corresponding to but slightly larger than said maximum transverse cross-section of said anchor body, a proximal end and a distal end, a plurality of circumferentially-spaced longitudinal first slots in said shaft, said slots extending proximally from said distal end along said shaft and sized to accommodate the barbs of an anchor received in said axial bore;

at least one longitudinal second slot in said shaft, said at least one slot extending proximally from said distal end along said shaft and sized to accommodate the object attached to said attachment means of an anchor received in said axial bore; and an elongated, solid shaft longer than said hollow shaft having a second longitudinal axis and a cross-section transverse to said second longitudinal axis corresponding to but slightly smaller than the cross-section of said axial bore in said hollow shaft, said solid shaft being adapted for insertion into and through said hollow shaft.

13. The system of claim 12 wherein said tool is formed of stainless steel.

14. The system of claim 12 wherein said object comprises a suture.

15. The system of claim 14 wherein at least two lengths of suture emanate from said anchor, and further wherein said tool comprises at least two longitudinal second slots.

16. The system of claim 12 wherein each of said shafts has a proximal end, and a handle is attached to each of said proximal ends of said shafts.

17. The system of claim 16 wherein said handles matingly engage each other when said shafts are oriented with respect to each other in at least one use position.

18. The system of claim 12 wherein said solid shaft includes a distal end and wherein the portion of said solid shaft adjacent said distal end has a transverse cross-section smaller than the transverse cross-section of the remainder of said solid shaft.

19. The system of claim 11 wherein portions of said object are attached to said attachment means and wherein said tool comprises:

an elongated, rigid shaft, said shaft including a distal end, a proximal end, a first small diameter portion adjacent said distal end and a second intermediate diameter portion located between said first small diameter portion and the remainder of said shaft, said second intermediate diameter portion defining capturing means disposed about the outer surface of said intermediate portion;

a deformable, tubular sleeve having a second distal end, a second proximal end, walls having a thickness approximately equal to the difference between the radius of said intermediate portion and the radius of said remainder portion of said shaft, and a length smaller than the combined length of said small diameter portion and said intermediate diameter portion of said shaft;

a counterbore formed in said distal end of said sleeve and adapted to receive said anchor body;

a plurality of circumferentially-spaced longitudinal radial slots in said sleeve, said slots extending proximally from said second distal end along said sleeve, said slots being adapted to receive the barbs of an anchor engaging said installation tool and said object attached to said attachment means, and
a rib located substantially adjacent said proximal end of said sleeve, said rib extending inwardly from said wall of said sleeve;
said sleeve being mounted about said intermediate diameter portion of said shaft such that in a first position the rib extends inwardly from the wall of the sleeve and engages said capturing means of said intermediate portion of said shaft, and in a second position said proximal end of said sleeve abuts said remainder portion of said shaft.

20. The system of claim 19 wherein said capturing means comprises a groove formed in the outer surface of said intermediate portion of said shaft.

21. The system of claim 19 wherein said capturing means comprises a pair of spaced projections formed on the outer surface of said said intermediate portion of said shaft.

22. Apparatus for deploying an anchor of the sort comprising a body and at least two barbs, said body having a longitudinal axis, a maximum cross-section transverse to said longitudinal axis slightly smaller than the transverse cross-section of said hole, a distal portion having an inner end and an outer end, a proximal portion having an inner end and an outer end, and a middle portion joining said inner end of said distal portion and said inner end of said proximal portion, said middle portion and said proximal portion together defining at least two equally-circumferentially-spaced channels extending inwardly from an axial projection of said maximum transverse cross-section of said distal portion, said channels extending longitudinally from said inner end of said distal portion to said outer end of said proximal portion, each of said channels having a base which is substantially parallel to said longitudinal axis in said middle portion and which slants outwardly relative to said longitudinal axis as it extends from said inner end of said proximal portion to said outer end of said proximal portion, said channels being separated by longitudinal walls extending radially outwardly from said longitudinal axis to an outer surface located on said axial projection of said maximum transverse cross-section, one of said barbs extending axially and radially outwardly from said inner end of said distal portion adjacent the base of each of said channels to an outer end located radially outwardly of said axial projection of said maximum transverse cross-section, each said barb being curved in its normal unrestrained state but capable of being deformed into a substantially straight configuration, and attachment means associated with said second portion for connecting an object to said anchor, said apparatus comprising:
an installation tool comprising:
an elongated, hollow shaft having a longitudinal axis, an axial bore having a cross-section transverse to said longitudinal axis corresponding to but slightly larger than said maximum transverse cross-section of said anchor body, a proximal end and a distal end,
a plurality of circumferentially-spaced longitudinal first slots in said shaft, said slots extending proximally from said distal end along said shaft, said slots being sized to accommodate the barbs of an anchor engaged by said tool;
at least one longitudinal second slot in said shaft, said at least one slot being sized to accommodate an object attached to said attachment means; and
plunger means including an elongated, solid shaft longer than said hollow shaft having a second longitudinal axis and a cross-section transverse to said second longitudinal axis corresponding to but slightly smaller than the cross-section of said axial bore in said hollow shaft, said solid shaft being adapted for insertion into and through said hollow shaft, whereby when said middle and proximal portions of said anchor body are received and held within said axial bore at said distal end of said shaft, said plunger means may be brought into engagement with said outer end of said proximal portion of said anchor body and be utilized to expel said anchor from said hollow shaft and to drive said anchor into said hole.

23. Apparatus for deploying an anchor of the sort comprising a body and at least two barbs, said body having a longitudinal axis, a maximum cross-section transverse to said longitudinal axis slightly smaller than the transverse cross-section of said hole, a distal portion having an inner end and an outer end, a proximal portion having an inner end and an outer end, and a middle portion joining said inner end of said distal portion and said inner end of said proximal portion, said middle portion and said proximal portion together defining at least two equally-circumferentially-spaced channels extending inwardly from an axial projection of said maximum transverse cross-section of said distal portion, said channels extending longitudinally from said inner end of said distal portion to said outer end of said proximal portion, each of said channels having a base which is substantially parallel to said longitudinal axis in said middle portion and which slants outwardly relative to said longitudinal axis as it extends from said inner end of said proximal portion to said outer end of said proximal portion, said channels being separated by longitudinal walls extending radially outwardly from said longitudinal axis to an outer surface located on said axial projection of said maximum transverse cross-section, one of said barbs extending axially and radially outwardly from said inner end of said distal portion adjacent the base of each of said channels to an outer end located radially outwardly of said axial projection of said maximum transverse cross-section, each said barb being curved in its normal unrestrained state but capable of being deformed into a substantially straight configuration, and attachment means associated with said second portion for connecting an object to said anchor, said apparatus comprising:
an installation tool comprising:
an elongated, rigid shaft, said shaft including a distal end, a proximal end, a first small diameter plunger portion adjacent said distal end and a second intermediate diameter portion located between said first small diameter plunger portion and the remainder of said shaft, said second intermediate diameter portion defining capturing means disposed about the outer surface of said intermediate portion of said shaft;
tubular means associated with said distal and intermediate portions said shaft adapted to receive and hold said middle and proximal portions of said anchor body, said tubular means including:
a deformable, tubular sleeve having a second distal end, a second proximal end, walls having a thickness approximately equal to the difference between the radius of said intermediate portion and the radius of said remainder portion of said shaft, and a length smaller than the combined length of said small diameter portion and said intermediate diameter portion of said shaft;

a counterbore formed in said distal end of said sleeve and adapted to receive said anchor body;

a plurality of circumferentially-spaced longitudinal slots in said sleeve, said slots extending proximally from said second distal end along said sleeve, said slots being adapted to receive the barbs of an anchor engaging said installation tool and an object attached to said attachment means, and a rib located substantially adjacent said proximal end of said sleeve, said rib extending inwardly from said wall of said sleeve;

said sleeve being mounted about said intermediate diameter portion of said shaft such that in a first position the rib extends inwardly from the wall of the sleeve and engages said capturing means disposed about the outer surface of said intermediate portion of said shaft, and in a second position said proximally end of said sleeve abuts said remainder portion of said shaft, whereby when said middle and proximal portions of said anchor are received and held within said tubular means adjacent said second distal end thereof, said distal end of said shaft may be brought into engagement with said outer end of said proximal portion of said anchor body and be utilized to expel said anchor from said tubular means and to drive said anchor into said hole.

24. A method for attaching an object to a workpiece comprising:
(a) providing:
1) means for forming a hole in said workpiece;
2) an anchor assembly comprising a body and at least two barbs;
said body having a longitudinal axis, a maximum cross-section transverse to said longitudinal axis slightly smaller than the transverse cross-section of said hole, a distal portion having an outer end and an inner end, a proximal portion having an inner end and an outer end, and a middle portion joining said inner end of said distal portion and said inner end of said second portion;
said middle portion and said proximal portion together defining at least two equally-circumferentially-spaced channels extending inwardly from an axial projection of said maximum transverse cross-section of said distal portion, said channels extending longitudinally from said inner end of said distal portion to said outer end of said proximal portion, each of said channels having a base which is substantially parallel to said longitudinal axis in said middle portion and which slants outwardly relative to said longitudinal axis as it extends from said inner end of said proximal portion to said outer end of said proximal portion, said channels being separated by longitudinal walls extending radially outwardly from said longitudinal axis to an outer surface located on said axial projection of said maximum transverse cross-section;
one of said barbs extending axially and radially outwardly from said inner end of said distal portion adjacent the base of each of said channels to an outer end located radially outwardly of said axial projection of said maximum transverse cross-section, each said barb being curved in its normal, unrestrained state but capable of being deformed into a substantially straight configuration; and
attachment means associated with said second portion for connecting an object to said anchor assembly; and
3) an installation tool for deploying said anchor in said hole in said workpiece, said tool comprising an elongated shaft having a longitudinal axis, a distal end and a proximal end;
tubular means associated with said distal end of said shaft adapted to receive and hold said middle and proximal portions of said anchor body; and
plunger means adapted for engagement with said outer end of said proximal portion of said anchor body, said plunger means being axially movable through said tubular means so as to expel said anchor from said tubular means and to drive said anchor into said hole;
b) forming a hole in a surface of said workpiece with said hole forming means;
c) aligning said longitudinal axis of said anchor body with said longitudinal axis of said shaft;
d) slidably engaging said middle and proximal portions of said anchor body with said tubular means;
e) inserting said distal portion of said anchor body into said hole such that said tubular means engages said workpiece adjacent said hole;
f) moving said plunger means through said tubular means so as to expel said anchor therefrom and so as to drive said anchor into said hole;
g) withdrawing said plunger from said hole and said tubular means from its engagement with said workpiece; and
h) attaching said object to said attachment means.

25. The method of claim 24 wherein step (b) occurs at any point prior to step (e).

26. The method of claim 24 wherein said attachment means comprises an opening extending transverse relative to said longitudinal axis of said anchor body through said proximal portion of said anchor body, and further including the step of threading one cord-like member through said opening prior to step (d) such that said cord-like member is securely attached to said proximal portion and at least one end of said cord-like member extends out of said hole after step (f).

27. The method of claim 24 wherein said object includes at least one attachment means-engaging portion, step (h) occurs prior to step (d), and said installation tool further comprises:
an elongated, hollow shaft having a longitudinal axis, an axial bore having a cross-section transverse to said longitudinal axis corresponding to but slightly larger than said maximum transverse cross-section of said anchor body, a proximal end and a distal end,
a plurality of circumferentially-spaced longitudinal first slots in said shaft, said slots extending proximally from said distal end along said shaft, and adapted to receive the barbs of an anchor disposed in said tool;
at least one longitudinal second slot in said shaft, said at least one slot extending proximally from said distal end along said shaft and adapted to receive said object attached to said attachment means, and an elongated, solid shaft longer than said hollow shaft having a second longitudinal axis and a cross-section transverse to said second longitudinal axis corresponding to but slightly smaller than the cross-section of said axial bore in said hollow shaft, said solid shaft being adapted for insertion into and through said hollow shaft.

28. The method of claim 27 wherein said attachment means comprises an opening extending transversely relative to said longitudinal axis of said anchor body through said proximal portion of said anchor body, and further including the step of threading one end of a cord-like member through said bore prior to step (d) such that said cord-like member is securely attached to said proximal portion and at least one end of said cord-like member extends out of said hole after step (f).

29. The method of claim 24 wherein said object includes at least one attachment means engaging portion, step (h) occurs prior to step (d), and said installation tool further comprises:

an elongated, rigid shaft, said shaft including a distal end, a proximal end, a first small diameter portion adjacent said distal end and a second intermediate diameter portion located between said first small diameter portion and the remainder of said shaft, said second intermediate diameter portion defining capturing means disposed about the outer surface of said intermediate portion of said shaft;

a deformable, tubular sleeve having a second distal end, a second proximal end, walls having a thickness approximately equal to the difference between the radius of said intermediate portion and the radius of said remainder portion of said shaft, and a length smaller than the combined length of said small diameter portion and said intermediate diameter portion of said shaft;

a plurality of circumferentially-spaced longitudinal radial slots in said sleeve, said slots extending proximally from said second distal end along said sleeve and adapted to receive the barbs and suture of an anchor attached to said installation tool;

a rib located substantially adjacent said proximal end of said sleeve, said rib extending inwardly from said wall of said sleeve;

said sleeve being mounted about said intermediate diameter portion of said shaft such that in a first position the rib extends inwardly from the wall of the sleeve and engages said capturing means disposed about the outer surface of said intermediate portion of said shaft, and in a second position said proximal end of said sleeve abuts said remainder portion of said shaft.

30. The method of claim 29 wherein said attachment means comprises an opening extending transversely relative to said longitudinal axis of said anchor body through said proximal portion of said anchor body, and further including the step of threading one end of a cord-like member through said opening prior to step (d) such that said cord-like member is securely attached to said proximal portion and at least one end of said cord-like member extends out of said hole after step (f).

31. The method of claim 29 wherein said capturing means comprises a groove formed in the outer surface of said intermediate portion of said shaft.

32. The method of claim 29 wherein said capturing means comprises a pair of spaced projections formed on the outer surface of said intermediate portion of said shaft.

33. Apparatus for attaching an object to a workpiece comprising:

an anchor comprising a body and at least two barbs;

said body having a longitudinal axis, a maximum cross-section transverse to said longitudinal axis, a distal portion having an outer end and an inner end, a proximal portion having an outer end and an inner end, and a middle portion joining said inner end of said distal portion and said inner end of said proximal portion;

said middle portion and said proximal portion together defining at least two equally-circumferentially-spaced channels extending inwardly from an axial projection of said maximum transverse cross-section of said distal portion, said channels extending longitudinally from said inner end of said distal portion toward said outer end of said proximal portion, each of said channels having a base which is substantially parallel to said longitudinal axis in said middle portion and which slants outwardly relative to said longitudinal axis as it extending from said inner end of said proximal portion toward said outer end of said proximal portion, said channels being separated by longitudinal walls extending radially outwardly from said longitudinal axis to an outer surface located on said axial projection of said maximum transverse cross-section;

one of said barbs extending axially and radially outwardly from said inner end of said distal portion adjacent the base of each of said channels to an outer end located radially outwardly of said axial projection of said maximum transverse cross-section, each said barb being capable of being deformed so that its outer end is positioned closer to said axial projection of said maximum transverse cross-section; and attachment means associated with said proximal portion for connecting an object to said anchor.

34. Apparatus for deploying an anchor of the sort comprising a body and at least two barbs into a hole formed in bone, said body having a distal end, a proximal end terminating in a proximal end surface, a longitudinal axis, and a maximum cross-section transverse to said longitudinal axis slightly smaller than the transverse cross-section of said hole, said barbs extending axially and radially outwardly from said body to an outer end located radially outwardly of an axial projection of said maximum transverse cross-section, each said barb being capable of being deformed so that its outer end is positioned closer to said axial projection of said maximum transverse cross-section, and said body comprising attachment means for connecting an object to said anchor, said apparatus comprising:

an installation tool comprising:

an elongated shaft having a longitudinal axis, a first distal end and a first proximal end;

tubular means associated with said distal end of said shaft adapted to receive and hold said proximal end of said anchor body and to allow said distal end of said anchor body to extend distally from said tubular means, said tubular means comprising a tubular element having a longitudinal axis substantially aligned with the longitudinal axis of said shaft, a second proximal end surrounding the portion of said shaft adjacent said first distal end and a maximum cross-section transverse to its longitudinal axis larger than the cross-section of said hole, whereby when the proximal end of an anchor is received and held by said tubular means, the distal end of said anchor can be positioned within said bone hole and said second distal end of said tubular means will reside outside and bear against the bone adjacent said bone hole; and plunger means adapted for engagement with said proximal end surface of said anchor body, said plunger means being axially movable through said tubular means so as to expel said anchor from said tubular means and to drive said anchor into said hole, said plunger means being adapted to extend out of the distal end of said tubular means and into said hole when driving said anchor into said hole.

35. Apparatus according to claim 34 wherein said tubular means are mounted to said shaft, said plunger means are formed at said distal end of said shaft, and said tubular means are free to rotate circumferentially about said shaft.

36. Apparatus according to claim 34 wherein the portion of said shaft adjacent said distal end of said shaft has a maximum cross-section transverse to said longitudinal axis smaller than the transverse cross-section of said hole.

* * * * *

UNITED STATES PATENT AND TRADEMARK OFFICE
CERTIFICATE OF CORRECTION

PATENT NO. : 5,217,486

DATED : June 8, 1993

INVENTOR(S) : John T. Rice et al.

It is certified that error appears in the above-indentified patent and that said Letters Patent is hereby corrected as shown below:

Claim 23, column 20, line 45, insert a comma after the word "normal";

Claim 26, column 22, line 45, after the word "one" and before the word "cord-like" insert the phrase --end of a--.

Signed and Sealed this

Fourth Day of April, 1995

Attest:

BRUCE LEHMAN

*Attesting Officer*  *Commissioner of Patents and Trademarks*